United States Patent
Feldman et al.

(10) Patent No.: US 12,042,273 B2
(45) Date of Patent: Jul. 23, 2024

(54) SYSTEM AND METHOD FOR NON-INVASIVE MONITORING OF BLOOD CONDITIONS

(71) Applicant: YISSUM RESEARCH DEVELOPMENT COMPANY OF THE HEBREW UNIVERSITY OF JERUSALEM LTD, Jerusalem (IL)

(72) Inventors: Yuri Feldman, Jerusalem (IL); Paul Ben-Ishai, Modiin (IL); Saul Yedgar, Jerusalem (IL); Gregory Barshtein, Jerusalem (IL); Andreas Caduff, Schmerikon (CH)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 271 days.

(21) Appl. No.: 16/083,955

(22) PCT Filed: Mar. 22, 2017

(86) PCT No.: PCT/IL2017/050357
§ 371 (c)(1),
(2) Date: Sep. 11, 2018

(87) PCT Pub. No.: WO2017/163245
PCT Pub. Date: Sep. 28, 2017

(65) Prior Publication Data
US 2020/0113495 A1    Apr. 16, 2020

Related U.S. Application Data

(60) Provisional application No. 62/312,038, filed on Mar. 23, 2016.

(51) Int. Cl.
*A61B 5/145* (2006.01)
*A61B 5/0507* (2021.01)

(52) U.S. Cl.
CPC ........ *A61B 5/14532* (2013.01); *A61B 5/0507* (2013.01); *A61B 5/14546* (2013.01)

(58) Field of Classification Search
CPC ...... A61B 5/0075; A61B 5/0082–0091; A61B 5/0507; A61B 5/14532;
(Continued)

(56) References Cited

U.S. PATENT DOCUMENTS 9,247,905 B2 * 2/2016 Caduff ................. A61B 5/0531
2006/0170931 A1 * 8/2006 Guo ..................... G01N 21/45
356/480

(Continued)

OTHER PUBLICATIONS

Bao, J., Davis, C., & Swicord, M. (1994). Microwave dielectric measurements of erythrocyte suspensions. Biophysical Journal, 66(6), 2173-2180. doi:10.1016/s0006-3495(94)81013-6 (Year: 1994).*

(Continued)

*Primary Examiner* — Benjamin S Melhus
*Assistant Examiner* — Samuel C Kim
(74) *Attorney, Agent, or Firm* — BROWDY AND NEIMARK, P.L.L.C.

(57) ABSTRACT

A system is presented for non-invasive monitoring one or more blood conditions of a media in a region of interest. The system comprises: a sensor device comprising at least one antenna sensor configured to be placed in the vicinity of the media and configured and operable to generate antenna beams of different frequencies in a frequency range of about 100 MHz to 90 GHz, receive radiation responses from the medium, and generate corresponding sensing data; and a control unit configured to receive and process said sensing data to determine a dielectric spectrum of the media indica-
(Continued)

tive of dielectric response of cytoplasm containing cells (red blood cells) in the media and determine one or more blood conditions.

9 Claims, 12 Drawing Sheets

(58) Field of Classification Search
CPC  A61B 5/14546–1464; G01J 3/00; G01J 3/28; G01J 3/42–457; G01J 2003/003; G01J 2003/2859; G01J 2003/2863; G01N 27/026

See application file for complete search history.

(56) References Cited

U.S. PATENT DOCUMENTS

| | | | |
|---|---|---|---|
| 2009/0275814 A1 | 11/2009 | Watanabe et al. | |
| 2009/0312615 A1* | 12/2009 | Caduff | A61B 5/0531 600/347 |
| 2013/0225960 A1 | 8/2013 | Porch et al. | |
| 2014/0213870 A1 | 7/2014 | Hsu et al. | |
| 2016/0169746 A1* | 6/2016 | Koyama | G01J 5/0837 250/338.1 |

OTHER PUBLICATIONS

Karacolak, T., Moreland, E. C., & Topsakal, E. (2013). Cole-cole model for glucose-dependent dielectric properties of blood plasma for continuous glucose monitoring. Microwave and Optical Technology Letters, 55(5), 1160-1164. doi:10.1002/mop.27515 (Year: 2013).*

Sun, T., et al. (2006). Dielectric spectroscopy of single cells: Time Domain analysis using Maxwell's mixture equation. Journal of Physics D: Applied Physics, 40(1), 1-8. https://doi.org/10.1088/0022-3727/40/1/s01 (Year: 2006).*

Havriliak, S.; Havriliak, S. J. (1996). Comparison of the havriliak-negami and stretched exponential functions. Polymer, 37(18), 4107-4110. doi.org/10.1016/0032-3861(96)00274-1 (Year: 1996).*

Leonid Livshits, Andreas Caduff, Mark S. Talary, Hans U. Lutz, Yoshihito Hayashi, Alexander Puzenko, Andrey Shendrik, and Yuri Feldman,. The role of GLUT1 in the sugar-induced dielectric response of human erythrocytes. J. Phys. Chem. B 113, 2212-2220 (2009).

Waldenberger, P., Fraedrich, G., Mallouhi, A., Jaschke, W. R., Perkmann, R., ung, T., and Czermak, B. V. (2003) Emergency endovascular treatment of traumatic aortic arch rupture with multiple arch vessel involvement, J Endovasc Ther 10, 728-732.

Polevaya, Y., Ermolina, I., Schlesinger, M., Ginzburg, B. Z., and Feldman, Y. (1999) Time domain dielectric spectroscopy study of human cells. II. Normal and malignant white blood cells, Biochim Biophys Acta 1419, 257-271.

Caduff, A., Livshits, L., Hayashi, Y., and Feldman, Y. (2004) Cell membrane response on D-glucose studied by dielectric spectroscopy. Erythrocyte and ghost suspensions, Journal of Physical Chemistry B 108, 13827-13830.

Hayashi, Y., Katsumoto, Y., Oshige, I., Omori, S., Yasuda, A., and Asami, K. (2009) The effects of erythrocyte deformability upon hematocrit assessed by the conductance method, Physics in Medicine and Biology 54, 2395-2405.

Livshits, L., Caduff, A., Talary, M. S., and Feldman, Y. (2007) Dielectric response of biconcave erythrocyte membranes to D- and L-glucose, Journal of Physics D-Applied Physics 40, 15-19.

Doctor, A., and Spinella, P. (2012) Effect of processing and storage on red blood cell function in vivo, Semin Perinatol 36, 248-259.

Bosman J. G. (2013) Survival of red blood cells after transfusion: processes and consequences. Front Physiol., 18:376.

Koshkaryev, A., Zelig, O., Manny, N., Yedgar, S., and Barshtein, G. (2009) Rejuvenation treatment of stored red blood cells reverses storage-induced adhesion to vascular endothelial cells, Transfusion 49, 2136-2143.

Yodh, A., and Chance, B. (1995) Spectroscopy and imaging with diffusing light, Physics Today 48, 34-40.

Basey-Fisher, T. H., Guerra, N., Triulzi, C., Gregory, A., Hanham, S. M., Stevens, M. M., Maier, S. A., and Klein, N. (2014) Microwaving blood as a non-destructive technique for hemoglobin measurements on microlitre samples, Adv Healthc Mater 3, 536-542.

Shiv, K. & Jaspal, S. 2013. "Measuring Blood Glucose Levels with Microwave Sensor", International Journal of Computer Applications, 72(15): 4-9. XP002771051.

Jean, B. R., et al. 2008, "Microwave frequency sensor for non-invasive blood-glucose measurements", SAS2008—Proceedings IEEE Sensors Applications Symposium: 4-7. XP002771052.

Fuchs et al., K., "Molecular Dynamics of Carbohydrate Aqueous Solutions. Dielectric Relaxation as a Function of Glucose and Fructose Concentration", Journal of Physical Chemistry Part B: Condensed Matter, Materials, Surfaces, Interfaces & Biophysical, 105(10): 2036-2042. XP055454850 (2001).

* cited by examiner

SYSTEM AND METHOD FOR NON-INVASIVE MONITORING OF BLOOD CONDITIONS

TECHNOLOGICAL FIELD

The present invention is generally in the field of non-invasive medical applications, and relates to a system and method for non-invasive monitoring of blood conditions.

BACKGROUND ART

References considered to be relevant as background to the presently disclosed subject matter are listed below:

[1] Leonid Livshits, Andreas Caduff, Mark S. Talary, Hans U. Lutz, Yoshihito Hayashi, Alexander Puzenko, Andrey Shendrik, and Yuri Feldman, J. Phys. Chem. B 113, 2212-2220 (2009).

[2] Waldenberger, P., Fraedrich, G., Mallouhi, A., Jaschke, W. R., Perkmann, R., Jung, T., and Czermak, B. V. (2003) Emergency endovascular treatment of traumatic aortic arch rupture with multiple arch vessel involvement, J Endovasc Ther 10, 728-732.

[3] Polevaya, Y., Ermolina, I., Schlesinger, M., Ginzburg, B. Z., and Feldman, Y. (1999) Time domain dielectric spectroscopy study of human cells. II. Normal and malignant white blood cells, Biochim Biophys Acta 1419, 257-271.

[4] Caduff, A., Livshits, L., Hayashi, Y., and Feldman, Y. (2004) Cell membrane response on D-glucose studied by dielectric spectroscopy. Erythrocyte and ghost suspensions, Journal of Physical Chemistry B 108, 13827-13830.

[5] Hayashi, Y., Katsumoto, Y., Oshige, I., Omori, S., Yasuda, A., and Asami, K. (2009) The effects of erythrocyte deformability upon hematocrit assessed by the conductance method, Physics in Medicine and Biology 54, 2395-2405.

[6] Livshits, L., Caduff, A., Talary, M. S., and Feldman, Y. (2007) Dielectric response of biconcave erythrocyte membranes to D- and L-glucose, Journal of Physics D-Applied Physics 40, 15-19.

[7] Doctor, A., and Spinella, P. (2012) Effect of processing and storage on red blood cell function in vivo, Semin Perinatol 36, 248-259.

[8] Bosman J. G. (2013) Survival of red blood cells after transfusion: processes and consequences. Front Physiol., 18:376.

[9] Koshkaryev, A., Zelig, O., Manny, N., Yedgar, S., and Barshtein, G. (2009) Rejuvenation treatment of stored red blood cells reverses storage-induced adhesion to vascular endothelial cells, Transfusion 49, 2136-2143.

[10] Yodh, A., and Chance, B. (1995) Spectroscopy and imaging with diffusing light, Physics Today 48, 34-40.

[11] Basey-Fisher, T. H., Guerra, N., Triulzi, C., Gregory, A., Hanham, S. M., Stevens, M. M., Maier, S. A., and Klein, N. (2014) Microwaving blood as a non-destructive technique for hemoglobin measurements on microlitre samples, Adv Healthc Mater 3, 536-542.

Acknowledgement of the above references herein is not to be inferred as meaning that these are in any way relevant to the patentability of the presently disclosed subject matter.

BACKGROUND

The disease of Diabetes has become the no. 3 killer in the Western World today. It is insidious, as it has no prior symptoms, no ill effects and is usually a result of life style, rather than pathogen. Its economic toll has reached staggering proportions, $245 billion in the US alone. However, it can be managed. Currently personal glucose levels are still controlled invasively by blood sampling. The worldwide market in 2008 was $8.8 billion and rising. Clinically constant oscillations in blood sugar levels lead to a cumulative negative effect on the health of the diabetic. Clearly the option of constant 24 hour monitoring of blood glucose levels would significant impact the wellbeing of diabetic patients and reduce the ever growing financial cost of the disease. However, with the invasive techniques of today (e.g. finger pricking), this is not possible.

The assessment red blood cell (RBC) functionality is instrumental for diagnosis and monitoring of clinical conditions, as well as for evaluation of the quality of packed red blood cell (PRBC) in the blood bank. The present regulations in the U.S. and Canada specify 42 days as the maximum shelf life for stored red blood cells (RBC). The overall degradation of PRBC quality is referred to as storage lesion. This include slowed metabolism, with a decrease in the concentration of adenosine triphosphate (ATP); oxidative damage, with changes to the structure of band 3 and lipid peroxidation; loss of function of cation-pumps and consequent loss of intracellular potassium and accumulation of sodium within the cytoplasm etc. The storage-induced damage to PRBC, which is noted already at the second week of storage and progresses with storage duration, has been shown to impair the functionality of PRBC, and to facilitate their removal from circulation following transfusion.

Studies with patients suffering from trauma or sepsis, or subjected to cardio-vascular surgical procedures, have shown that the survival rate of blood recipients was increased with decreased storage duration. Patients who were transfused with PRBC that had been stored longer than 14-21 days had higher rates of in-hospital mortality, intubation beyond 72 hours, renal failure, and sepsis or septicemia, and increased rate of composite of complications.

Various non-invasive techniques have been developed, e.g. pure optical techniques, photoacoustic techniques, impedance-based techniques, and dielectric spectroscopy based techniques.

Dielectric spectroscopy based measurements (or conductivity spectroscopy), in distinguish to the impedance based ones, utilize intrinsic electric material properties, such as the complex permittivity $\varepsilon^*(\omega)$ or conductivity $\sigma^*(\omega)$ spectra of the media under measurements, which are measured as a function of frequency of an external electromagnetic field being applied to the media. The impedance based techniques are focused mostly on the properties of electrode/material interfaces, and impedance spectra are taken under controlled DC voltage and current conditions.

GENERAL DESCRIPTION

The present invention is aimed at providing a non-invasive measurement of blood conditions (e.g. glucose concentration) in vivo and transdermal. The invention utilizes the principals of dielectric spectroscopy.

The inventors have found that proper use of dielectric spectroscopy provides for detection of one or more desired dispersion regions in the response of the media, i.e. complex permittivity of the media as a function of frequency of the external field. This provides for accurate determination of various blood conditions, such as glucose concentration, because the detected dispersion region(s) is/are indicative of the radiation response of the body regions carrying the media of interest.

More specifically, the technique of the invention, in some of its aspects, is based on the inventors' understanding that a change of the nature of the cytoplasm (liquid interior of RBC), which is an aqueous medium can be detected by measuring the dielectric spectrum of bulk water in the frequency range of about 0.5-60 GHz. At these frequencies, the spectrum is the result of almost only the water, both inside and outside the cellular membranes. Therefore, it is possible to filter out the effect of the plasma and see only the changes in the cytoplasm. These changes are indicative of a change in the cytoplasm glucose concentration.

Indeed, it should be understood that the liquid interior of a RBC, known as the cytoplasm, is an aqueous medium for the biological machinery that keeps the cell alive and allows it to perform its specified task. Clearly, any influence on the health of the cell affects the state of the cytoplasm as well. This is the case whether it is aging of the cell or an excess of glucose in the blood plasma. At these frequencies, the spectrum is the result of almost only the water, both inside and outside the cellular membranes. By the use of mixture formulas, it is possible to filter out the effect of the plasma and see only the changes in the cytoplasm. Large changes in glucose concentrations in blood plasma significantly change the nature of the cytoplasm in RBC in the same plasma. This change modifies the dielectric response of RBCs particularly in the frequency range 0.5 GHz to 60 GHz at a certain temperature (e.g. 37° C.).

The present invention, in one of its broad aspects, provides a system for non-invasive monitoring one or more blood conditions of a media in a region of interest, the system comprising: a sensor device comprising at least one electromagnetic radiation sensor configured to be placed in the vicinity of the media and configured and operable to generate two or more radiating beams of different frequencies in a frequency range of about 100 MHz to 90 GHz, receive radiation responses from the medium, and generate corresponding sensing data; and a control unit configured to receive and process said sensing data to determine a dielectric spectrum of the media indicative of dielectric response of cytoplasm containing cells (e.g. red blood cells) in said media and determine one or more blood conditions.

According to some embodiments of the present invention, there is provided a monitoring/measurement system for non-invasive measurements of blood parameters/conditions. The system comprises a sensor device including at least one electromagnetic radiation sensor, being antenna sensor (e.g. micro-strip antenna device) or resonator sensor, configured to enable its placement on a skin of a subject and configured and operable to generate two or more radiating beams (e.g. antenna beams) of different frequencies in a frequency range of about 0.5 GHz to 60 GHz, and receive radiation responses (reflection and/or transmission signal(s)) of the subject to said radiating beams being indicative of a dielectric spectrum of media in the near field region below the skin (cytoplasm region).

From this dielectric spectrum, blood glucose conditions (level or relative changes) can be determined by analyzing radiation response data (indicative of the received radiation responses, and extracting therefrom dielectric response of RBCs at a given temperature during the measurements.

It should be understood that for non-invasive measurements of blood related parameters of a subject, the radiation sensor has to be attached to the skin. In some embodiments, the radiation sensor is placed on the upper arm of a patient.

It should also be understood that such spectral response of the media can be obtained using the radiation sensor having a single radiation unit (e.g. antenna unit or resonator unit) configure and operable to selectively generate radiating beam of a different frequency, or by using two or more such units each operable with a different frequency.

In some embodiments there is provided a novel multi-sensor system for in vivo detection of blood conditions, e.g. glucose variation. Such multiple sensors may include the radiation sensor (antenna sensor or resonator), as well as one or more environmental condition sensors, e.g. temperature, humidity, etc. Thus, in some embodiments, the system may also comprise other sensor(s) configured to determine blood volume, temperature, skin moisture and others, to thereby enable to assess the effect of these parameters on the signal passing through the skin to sample the blood.

Thus, the measurement/monitoring system of the invention comprises: a sensor device including at least the above-described radiation sensor; and a control utility/unit for data analysis of the sensing data. The sensor device and the control utility may be integral in a single unit/device; or at least some of the data analyzing modules of the control utility are located in a remote device; or the entire control utility is an external to sensor device and connected thereto via wires or wireless signal transmission using technique(s) of any known suitable type. In case wireless communication is used, the sensor device is equipped with corresponding signal transmission/formatting utilities of any known suitable type.

In some embodiments, the some or all data analysis modules of the control unit may be incorporated in a personal electronic/communication device, such as a smart phone for data analysis and for external monitoring. To this end, such communication device may be installed with a specific software application. Such communication device may typically be located in the vicinity of the sensor device during measurements, and the communication between them may be Bluetooth or IR based.

According to other embodiments/aspects of the present invention, the invention is aimed at determining the quality and viability of RBC ex vivo, in a test tube/container, including PRBC in their intact bag (unit), without compromising the bag integrity. The invention relates to the use of dielectric spectroscopy in the region of the gamma dispersion (100 MHz-90 GHz) to determine/monitor the properties/quality/functionality of RBC by either RBC water condition/structure and/or glucose content. When applied to PRBC bag, the system comprises a radiation sensor (e.g. antenna) to be placed in close proximity or in contact with the PRBC-containing plastic bag. The radiation sensor is configured to generate at least one microwave signal in the frequency range of about 100 MHz to 90 GHz which penetrates the plastic bag, and to receive reflection from the media inside the bag including reflection from the blood cells. The reflected signal is indicative of the dielectric permittivity of the cytoplasm of the blood which enables to determine the viability of the blood that can be utilized as a marker for the quality of the blood in medical applications. The system may also comprise a sensor configured to determine the concentration of RBC. In some embodiments there is provided a system for non-invasive monitoring of quality and inventory of packaged red blood cells (PRBC), stored in a blood bank.

In this connection, it should be understood that currently there is no method of quality control of PRBCs, short of opening the package and taking a sample. This violates the integrity of the PRBC bag—which compromises it for medical application. Concurrently it is known that red blood cells have a life expectancy of no more than 42 days. As the cells age, the cellular membranes become distorted and rigid. The overall degradation of PRBC is referred to as storage lesion and includes various biochemical and biophysical alteration in cells properties. Prospective and retrospective clinical trials demonstrated that transfusion of "old" PRBC (storage time is high than 14-21 days) related to development of negative out-come in different types of transfusion recipients (septic, trauma, cardio-surgery etc.). At the moment, the inventory is maintained by a "first in, first out" policy and cannot take into account level of PRBC lesion. Any procedures for non-invasive (without blood sampling) monitoring of PRBC lesion has not been included in blood bank practices. Therefore, in blood bank inventory, there is a need to test whether a blood portion is viable and to maintain the integrity of the sample bag. Moreover, storage duration should not be the sole criteria for determining the quality of PRBC. Today, the functionality of PRBC is determined by the combination of its initial, donor-specific, characteristics, the blood banking procedures applied to the PRBC bag, and its storage duration. There is a need for specifically testing, the level of PRBC lesion in each individual bags for characterization of PRBC quality.

The present invention overcomes the above-mentioned problems by providing a technique in which a microwave signal penetrates a plastic bag containing a blood portion and is reflected from the blood cells. The reflected signal contains critical information about the viability of the blood that can be utilized as a marker for the quality of the blood in medical applications.

According to some embodiments of the present invention, there is provided a system comprising at least one sensor device and a control unit for processing sensing data. The at least one sensor device comprises at least one radiation sensor (e.g. antenna sensor) for locating in the vicinity of a blood-containing region and configured and operable to irradiate said region by electromagnetic radiation in a frequency range of about 100 MHz to 90 GHz, and receive at least one reflection response from said region, and generate corresponding sensing data, said sensing data being indicative of a dielectric spectrum of the media, thereby enabling to determine dielectric response of red blood cells in said media and determine one or more blood conditions.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
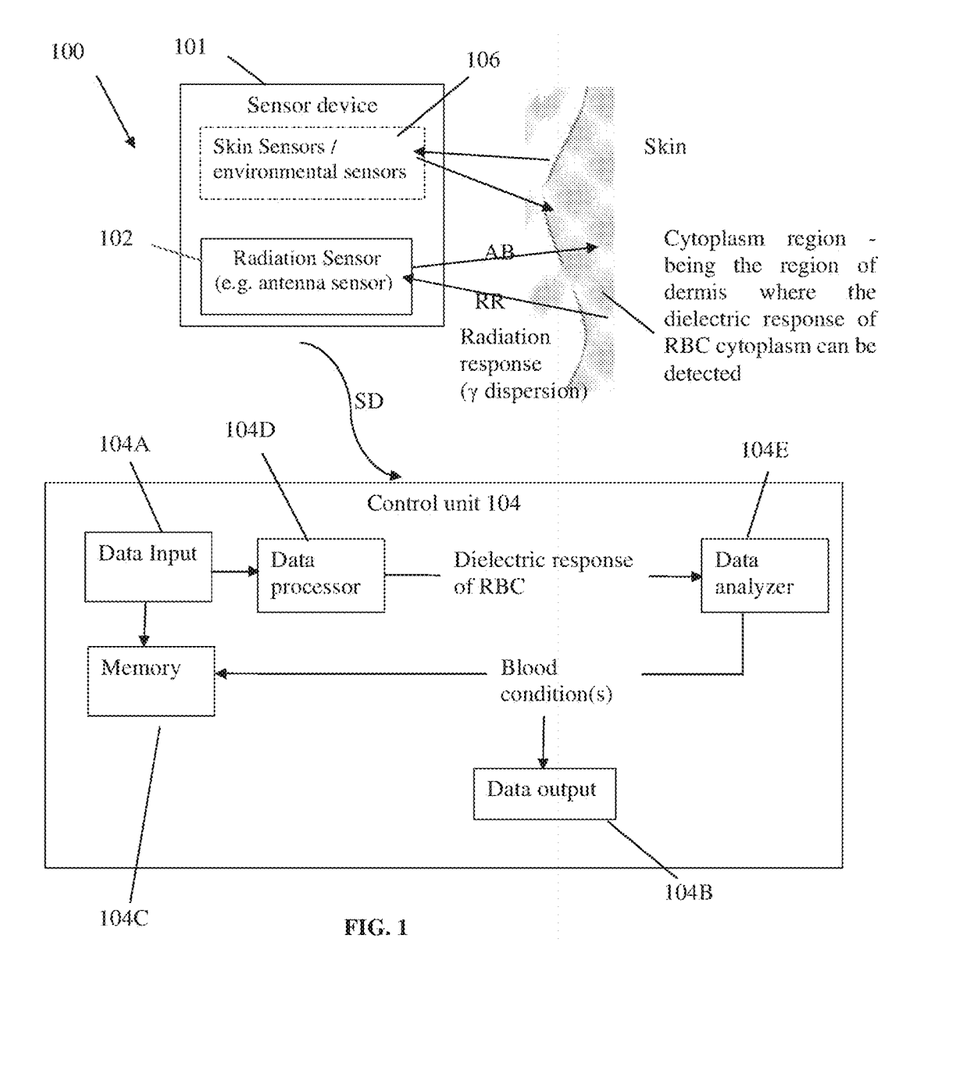
FIG. 1 is a block diagram of a monitoring/measurement system of the present invention, exemplified as being used for measurements on a subject's body.

Referring to FIG. 1, there is illustrated, by way of a block diagram, the main structural and functional parts of a monitoring (measurement) system 100 of the present invention. The system 100 is configured for non-invasive monitoring one or more blood conditions of media in a region of interest. In the figure, the embodiment of the system used for measurement on a patient's body is exemplified. The system 100 includes such main constructional parts as a sensor device 101 and a control unit 104. The sensor device may be attached to patient's skin at the upper arm.

The sensor device 101 includes a radiation sensor 102 (one or more sensor units) which is configured to be placed in the vicinity of the media under measurements. As shown in this example, the antenna sensor 102 may be placed on the skin. As also shown in the figure (by dashed lines), the sensor device 101 may include one or more other-type sensors, for example sensor(s) for measuring one or more environmental conditions, e.g. temperature, humidity, etc.

Generally, the radiation sensor 102 includes a transmitter of two or more beams/waves of different frequencies, and a receiver of radiation responses of different frequencies. The radiation sensor 102 may include one or more antenna units (each having transmitter and receiver), or one or more open resonators (each generating electromagnetic wave(s) of specific frequency(ies) or selecting specific frequency(ies) from a signal). The configuration and operation of an antenna unit, as well as open resonator, are generally known and need not be described in details, except to note that an open resonator in the simplest case includes two mirrors facing each other and its operation is based on interference effect based on multiple reflection of waves between two closely spaced and highly reflecting mirrors.

In the description below, the radiation sensor device used in the system of the invention is referred to as antenna device/sensor or antenna unit, and the radiation generated by the radiation sensor is described as antenna beams. However, it should be understood that the principles of the invention are not limited to this specific technique, and the radiation sensor device may alternatively or additionally include open resonator(s) configured using any known suitable technique.

Thus, the radiation sensor 102 is configured and operable to generate antenna beams AB of different frequencies in a frequency range of about 100 MHz to 90 GHz, receive radiation responses RR from the media, and generate corresponding sensing data SD. It should be understood that the antenna sensor may be configured for operation in transmission and/or reflection modes.

The control unit 104 is configured generally as a computing/electronic utility including inter alia such utilities as data input and output utilities 104A, 104B, memory 104C, and data processor and analyzer modules 104D, 104E. As will be described more specifically further below, the control unit 104 is configured to receive and process the sensing data SD to determine a dielectric spectrum of the media, to detect dielectric response of red blood cells in the media and determine one or more blood conditions, e.g. blood glucose concentration.

As indicated above, the antenna sensor irradiates the media by multiple beams of different frequencies, and the sensing data SD is therefore indicative of the radiation response of the media as a function of frequency. To this end, the antenna sensor may include one or more antenna units, each configured and operable for sequentially generating multiple antenna beams of the different frequencies in the predetermined frequency range; or may include a plurality of antenna units for generating a corresponding plurality of the antenna beams of the different frequencies in the predetermined frequency range.

As described above, the change of the nature of the cytoplasm can be detected non-invasively by measuring the dielectric spectrum of bulk water in the frequency range about 0.5-60 GHz. Cytoplasm region is the region of dermis where the dielectric response of RBC cytoplasm can be detected. The inventors have found that the dielectric response of the cytoplasm of RBC in the frequency range about 0.5 GHz to 60 GHz is due to water. This dielectric response of the cytoplasm of RBC is significantly modified by the addition of glucose to the blood plasma outside the cellular membrane.

Figure 2A:
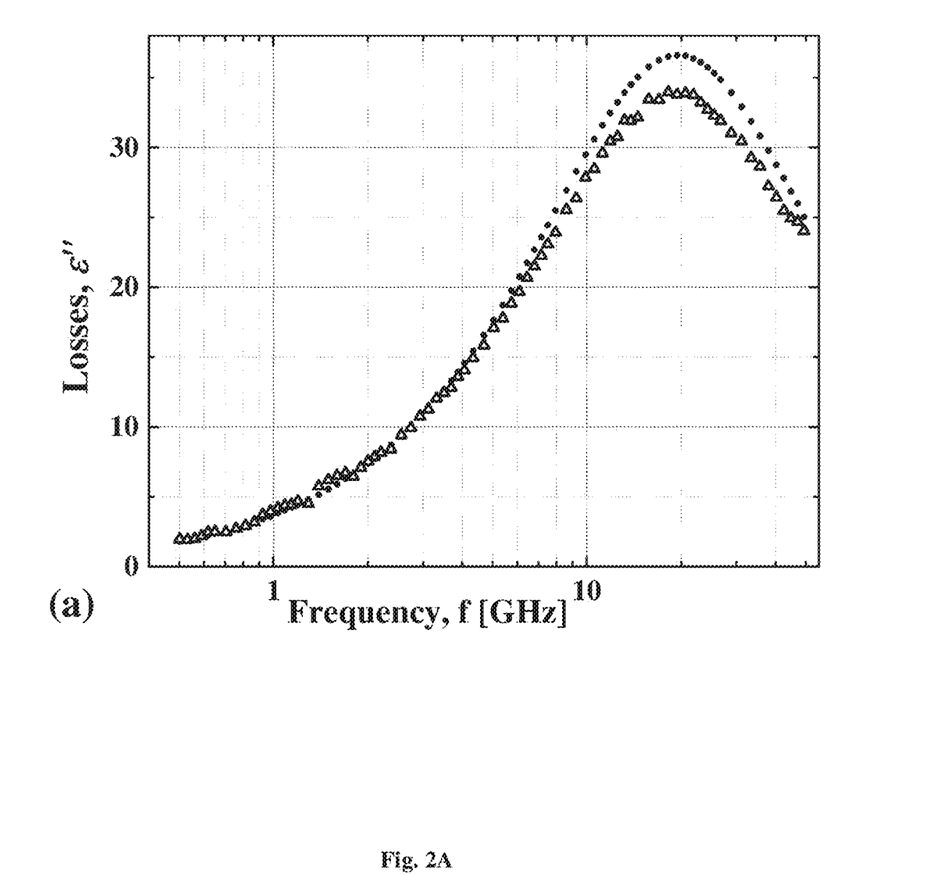
FIG. 2A shows a measured spectrum of RBCs suspension (triangle symbols) in comparison with bulk water dielectric loses (solid dot symbols), with DC conductivity being removed.

Reference is made to FIG. 2A showing the typical dielectric spectra of RBCs suspended in phosphate-buffered saline (PBS), compared with the dielectric spectra of pure water. The measurements were made at a constant temperature of 25° C. using an open-ended coaxial probe and Agilent PNA in the frequency region of 0.5 to 60 GHz. The raw spectra show a measurable change in both the broadening and position of the main relaxation peak. This peak is associated with the dielectric response of bulk water, found in the external buffer solution and inside the cytoplasm of the cells. Once the concentration of cells is known and the spectra of the buffer accounted for, one can extract the spectrum of the single cell by the application of a mixture formula.

Spectra were recalculated to one cell using Krashevski relationship (Journal of Applied Physics 47, 1275 (1976); doi: 10.1063/1.322825):

$$\varepsilon_{cyt} = \left( \frac{(\varepsilon_{mix})^{1/2} - (\varepsilon_{buff})^{1/2} \cdot \varphi_{buff}}{\varphi_{cyt}} \right)^2 \quad (1)$$

Figure 2B:
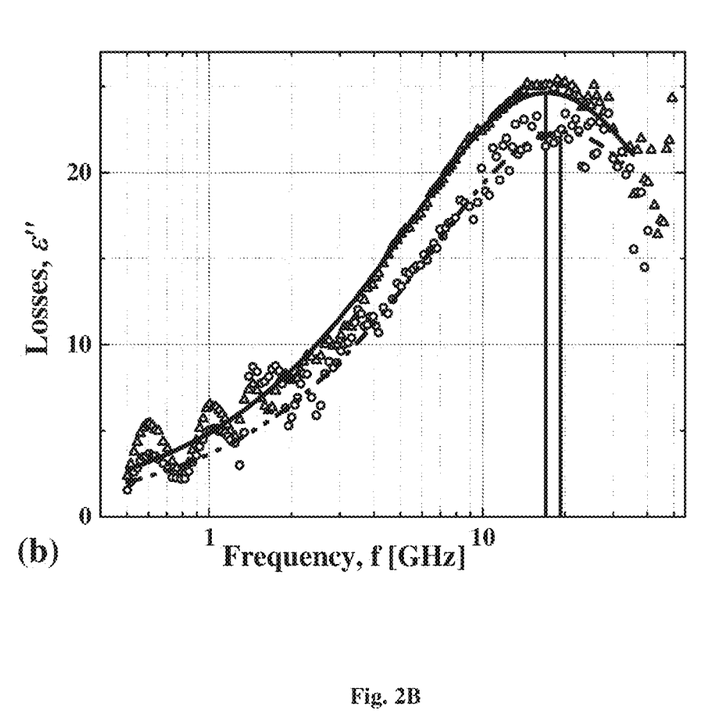
FIG. 2B shows the derived losses of cellular cytoplasm for 0 mM D-glucose (triangles) and 10 mM D-glucose (circles); the lines are the fitting curves.

In the frequency range measured, this can be assigned to the cytoplasm of the cell interior. The results are shown in FIG. 2B.

Figure 3:
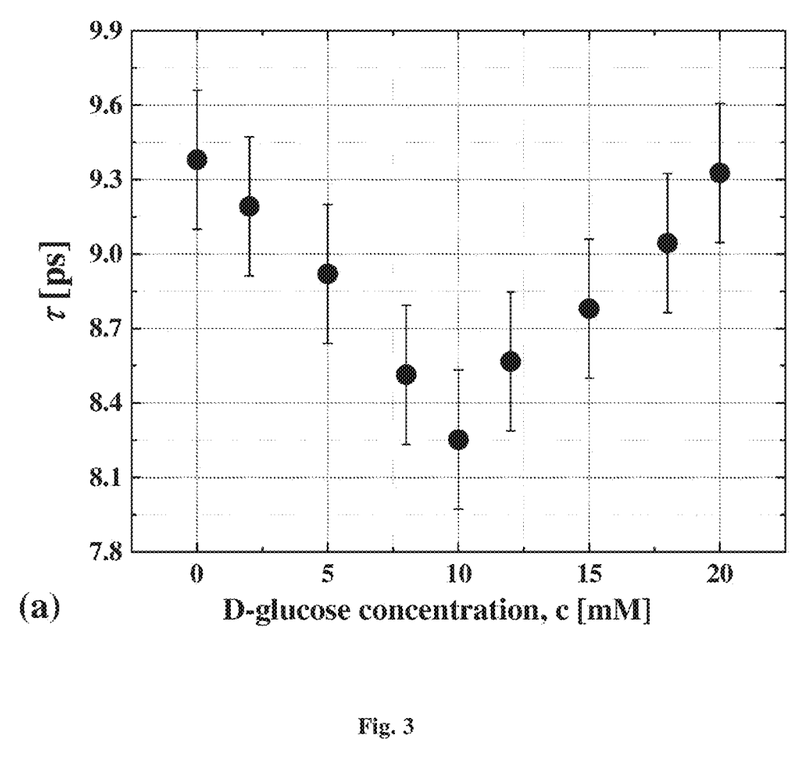
FIG. 3 shows the relaxation time as a function of concentration for the single cell spectra in the presence of varying buffer concentrations of D-glucose.
Figure 4:
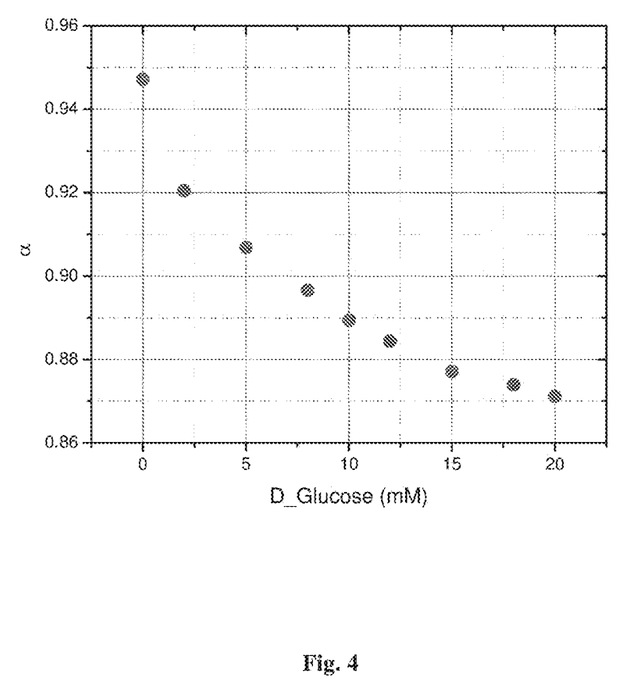
FIG. 4 shows a broadening parameter for the single cell spectra as a function of D-glucose concentration.

The single cell spectra, $\varepsilon^*(\omega)$, were fitted to the Cole-Cole dielectric function and a conductivity term:

$$\varepsilon^*(\omega) = \frac{\Delta\varepsilon}{1 + (i\omega\tau)^\alpha} + \frac{\sigma}{i\omega\varepsilon_0} + \varepsilon_\infty \quad (2)$$

where $\Delta\varepsilon$ is the dielectric strength, $\tau$ is the characteristic relaxation time, $\alpha$ is the broadening parameter, $\sigma$ is the dc conductivity, $\varepsilon_0$ is the permittivity of free space and $\varepsilon_\infty$ is the high frequency limit of the real component of the dielectric permittivity. By tracing the concentration-based behavior of these components, one can observe how the metabolism of the cell is affected by the PBS glucose concentration. The results are shown in FIGS. 3 and 4 for the relaxation time and the broadening parameter respectively.

The dip in the relaxation times at the concentration at 12 mM concentration of external glucose is significant because this concentration has been linked to the efficacy of adenosine triphosphate (ATP) in the regulation of the Glucose Transporter 1 (GLUT1) cellular transporter, responsible for the passage of glucose through the cell membrane and a main factor in diabetes [1]. The conclusion is that the dielectric response of the cytoplasm in this frequency range is due to the water therein and its interaction with ATP. This enables exploiting the dielectric response of the cytoplasm in this frequency range for the non-invasive monitoring of diabetes.

Figure 5:
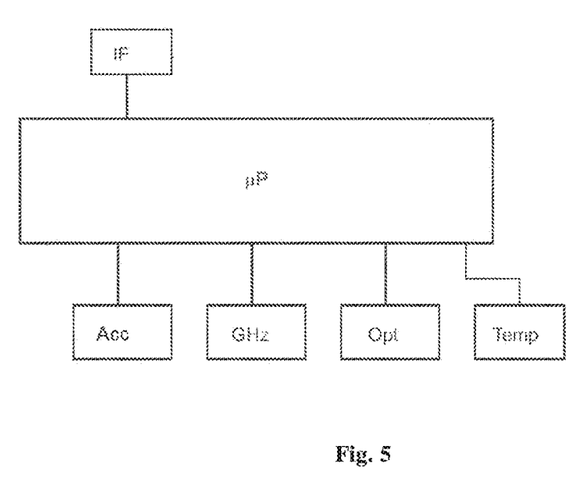
FIG. 5 illustrates a schematic block diagram of a possible configuration of the monitoring system of the present invention.
Figure 6:
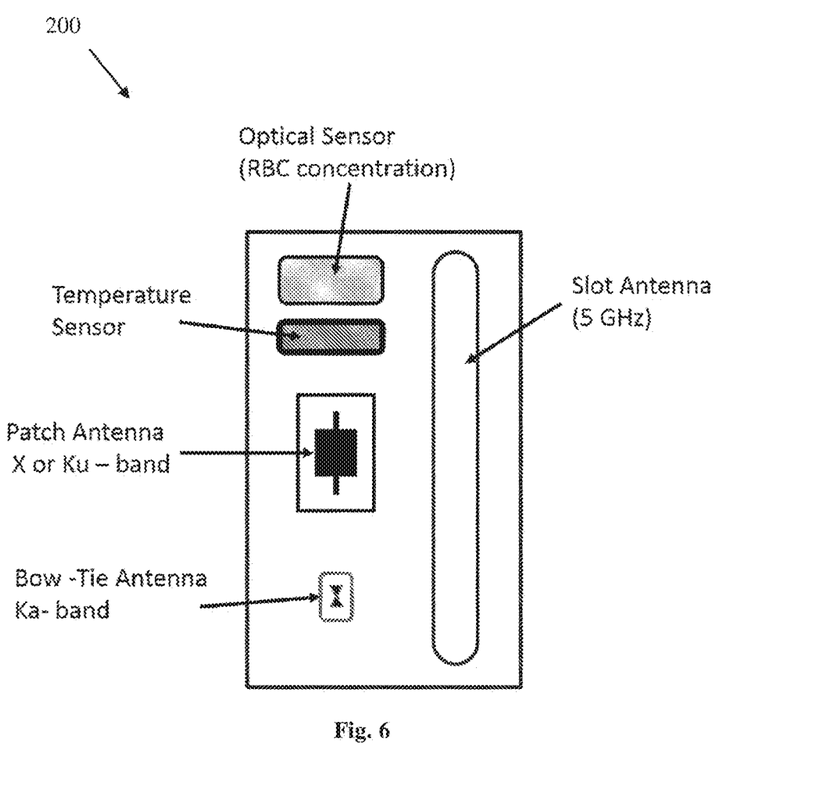
FIG. 6 schematically illustrates an example of a possible configuration of the monitoring multi-sensor system of the present invention.

In some embodiments, the system provides a multi-sensor platform 200 capable of sampling the capillary blood either in reflection mode or in transmission mode. Some configurations of the system are illustrated in FIGS. 5 and 6. In the specific and non-limiting example illustrated in FIG. 6, the antenna sensor comprises a dielectric module including a plurality of microstrip sensors. One sensor is configured and operable to discreetly probe the dielectric spectrum of the cytoplasm at frequencies in the range of about 0.5-60 GHz. The sensors may be combinations of micro strip, bow tie or other 2-dimensional shaped patch antenna, sensitive in the X, Ku and Ka frequency bands. The sensor may be configured as a micro strip line sensor for probing capillary blood. The system comprises another sensor configured and operable to measure temperature and optical sensors configured and operable to detect blood perfusion and RBC concentration combined with an acceleration meter. The module noted IF represents Interface to data communication capabilities.

Turning back to FIG. 1, the system also includes the control unit 104 receiving from the sensor(s) a raw dielectric signal. Artifacts introduced by temperature and surface water are taken into account using the results of an onboard temperature sensor 106. Signal loss due to absorption by water in the upper layers of the skin is accounted for by studying the low frequency dielectric response. The red blood cell concentration is accounted for optically using the concurrent information gain of blood perfusion. The control unit 104 (its data processor and analyzer modules 104D, 104E) uses equation (1) to obtain the full parameter of the single cell spectra. The control unit 104 comprises onboard memory utility 104C to store theses data points and calibrate them against glucose concentration of the patient. Sudden temporal changes to the patient's situation may be received by the control unit wirelessly, via a blue tooth connection and/or via a cellphone to the patient's physician.

Dielectric spectroscopy (DS) is a label free and non-invasive method and applicable to biological cells for characterization. In general, remarkable dielectric responses attributed to interfacial polarization are observed in the frequency region of so-called the β-dispersion for a cell suspension [2]. Previous DS studies show, for example, different dielectric properties of normal lymphocytes and leukemia cells [3] and change of the dielectric response for human erythrocyte with glucose concentration in the extracellular medium [4]. Sensitivity of DS to alteration of RBC membrane properties and intercellular composition has been previously shown [5, 6].

Studies of the dielectric response of the cellular cytoplasm for stored RBC reveal a dramatic change in the dielectric parameters as a function of age that can be correlated to changes to the cellular membrane. One of the markers to RBC aging and viability is the change in membrane properties. Changes throughout storage have the ability to affect membrane composition and integrity, which are both integral to the maintenance of RBC function. Compositional membrane changes can affect membrane fluidity, lipid sorting, bilayer thickness, and the packing efficiency of membrane components, factors that have the potential to affect RBC deformability. Compositional changes may also lead to changes in passive membrane permeability [7].

Figure 7A:
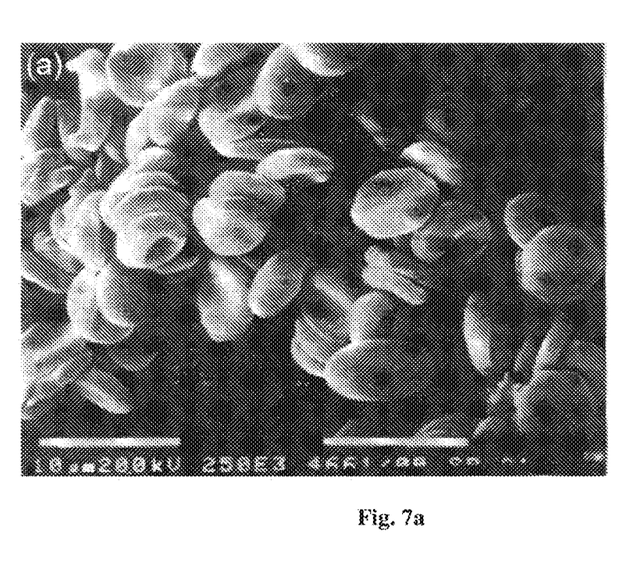
FIGS. 7a-7b shows a micrograph of stored red blood cells freshly taken (FIG. 7a) and after 21 days in storage (FIG. 7b).
Figure 7B:
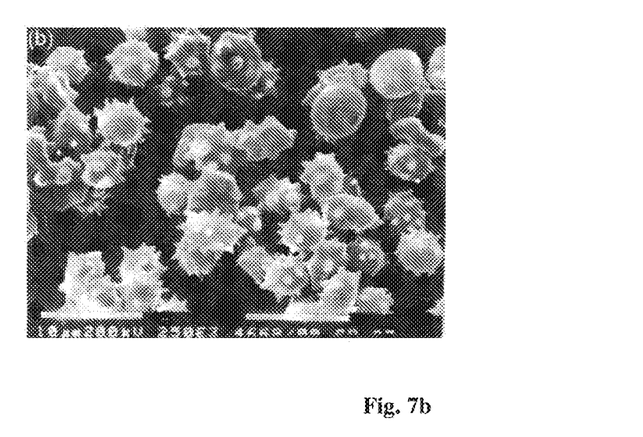

Membrane loss leads to critical, irreversible changes in shape and surface area: volume ratio which affects the gross morphology of RBCs and has serious implications for RBC deformability [7, 8]. The dramatic changes can be seen in the micrographs presented in FIGS. 7a-7b. FIG. 7a shows RBC freshly collected with the typical concave disk shape. The same cells are shown in FIG. 7b after 21 day storage. The membramatic change in the nature of the membrane is clearly visible.

Figure 8A:
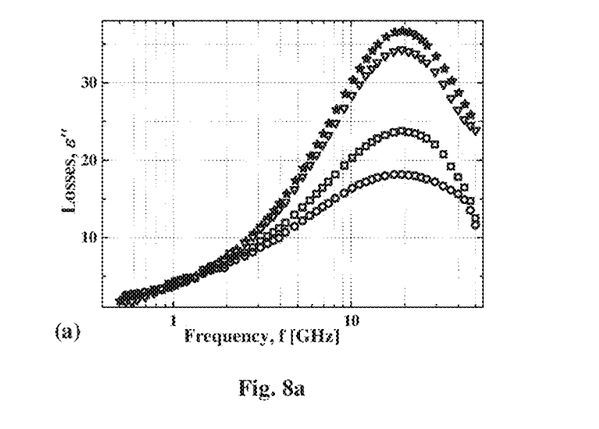
FIG. 8a-8b shows the dielectric loss spectra at 25° C. of fresh RBC suspension in the SAGM buffer (squares) and the derived losses of cellular cytoplasm for same sample (circles) compared to SAGM buffer (triangles) and water (stars), dc conductivity has been removed. In panel (b) shows the derived losses of cellular cytoplasm for fresh RBC (circles) and stored ones (triangles). The lines are the fitting curves.
Figure 8B:
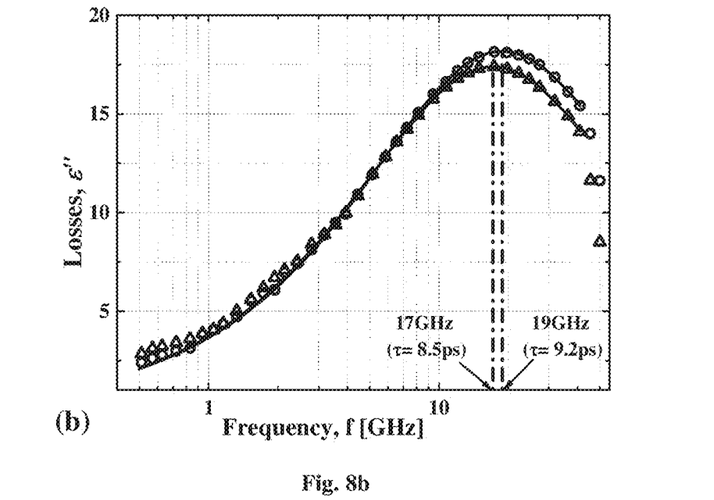

They are now distorted beyond recognition. In addition to membrane loss, in vitro metabolic and mechanical stresses can lead to disruption of the asymmetric phospholipids distribution of the cell membrane, resulting in phosphatidylserine (PS) externalization, which then acts as a signal for erythrophagocytosis by macrophages of the reticuloendothelial system [9]. Dielectric measurements of RBC suspensions in the frequency region of 100 MHz to 50 GHz as a function of aging also reveal a distinct time point after which the spectra are radically changed. Reference is made to FIG. 8a showing the spectra for the dielectric loss spectra at 25° C. of fresh RBC suspension in the SAGM buffer (squares) and the derived losses of cellular cytoplasm for same sample compared to SAGM buffer and water with removed dc conductivity. The FIG. 8b shows the derived losses of cellular cytoplasm for fresh RBC (circles) and stored ones (triangles). The lines are the fitting curves.

The measurements are of bulk samples of stored RBC in a buffer solution. Once the concentration of cells is known and the spectra of the buffer accounted for, one can extract the spectrum of the single cell. Spectra were recalculated to one cell using equation (1) above. In the frequency range measured this can be assigned to the cytoplasm of the cell interior. The spectra were fitted using the equation (2) above.

Figure 9:
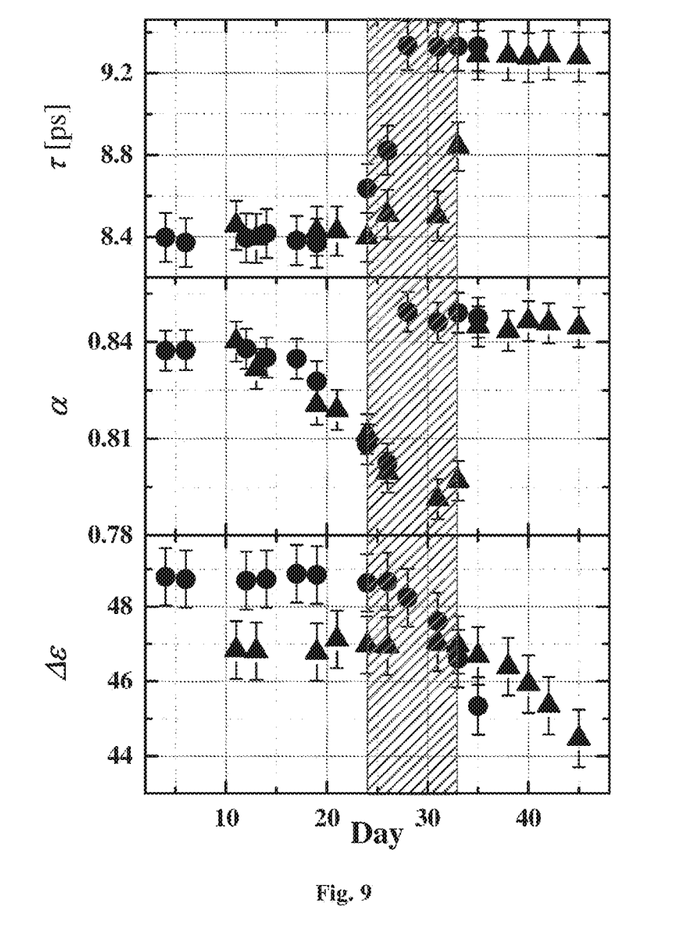
FIG. 9 shows the relaxations times, $\tau$, the broadening parameter $\alpha$ and the relaxation amplitude $\Delta\varepsilon$ of the Cole-Cole dielectric function as defined by equation (2), for two different samples as a function of storage time.
Figure 10A:
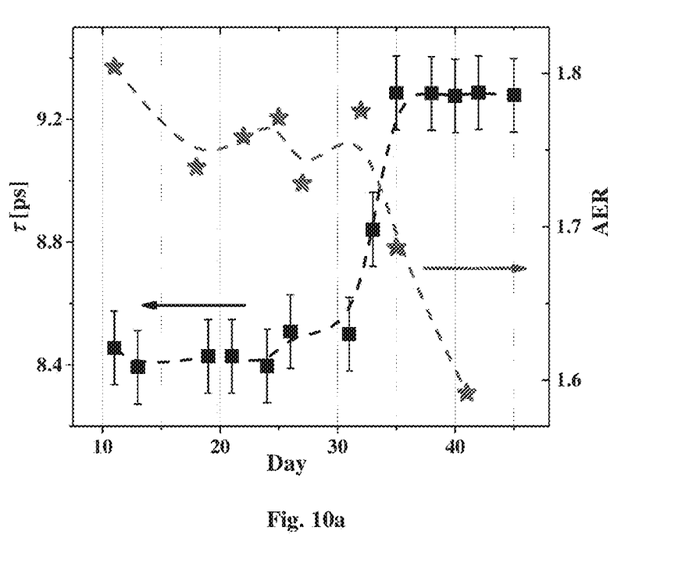
FIGS. 10a-10b show an average elongation ratio (Av Er i.e. The average ratio between the two radii of the ellipse) and the dielectric relaxation times of the same RBC for two different samples.
Figure 10B:
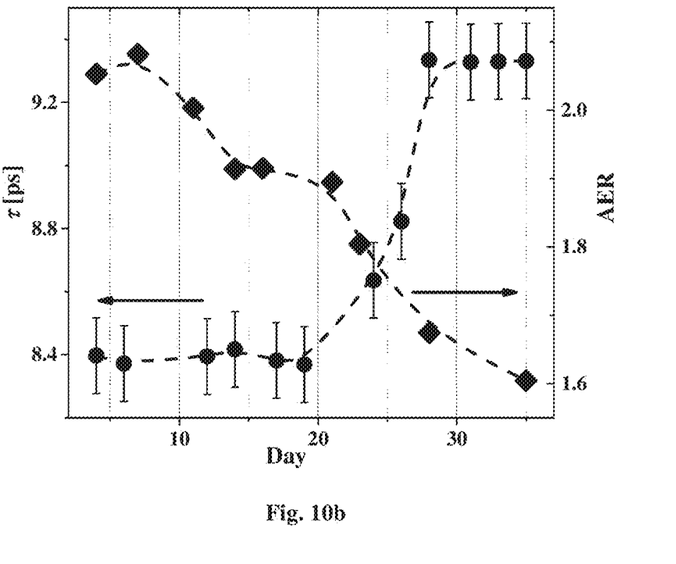

FIG. 9 shows the relaxations times, $\tau$, the broadening parameter $\alpha$ and the relaxation amplitude $\Delta\varepsilon$ of the Cole-Cole dielectric function as defined by equation (2), for two different samples as a function of storage time. Fitting parameters are very similar for all six samples represented in FIGS. 9, 10a-10b. The results show a distinct change in behavior at around 25-30 days, indicating a change in cell viability. This can be confirmed by comparing these parameters to recognized indicators of cellular change. FIGS. 10a-10b show an average elongation ratio (Av Er i.e. the average ratio between the two radii of the ellipse) and the dielectric relaxation times of the same RBC (FIG. 10a-10b) for two different samples. Both dielectric data and physiological data show the same critical times. Therefore, the system of the present invention allows non-invasive control of the quality of stored RBC in a blood bank and manages of the inventory.

The system and the method of the present invention provide data indicative of any given PRBC relative viability and thus prospective efficacy. This provides clinicians with actual data on PRBC quality when making decisions about which and how many bags of PRBCs to use for transfusion of a given patient. The present invention may be directed toward applications in PRBC quality control, as well as the disease diagnosis by quantifying PRBC dielectric properties via dielectric-spectroscopy in microwave diapason and subsequent computational analysis.

Figure 11:
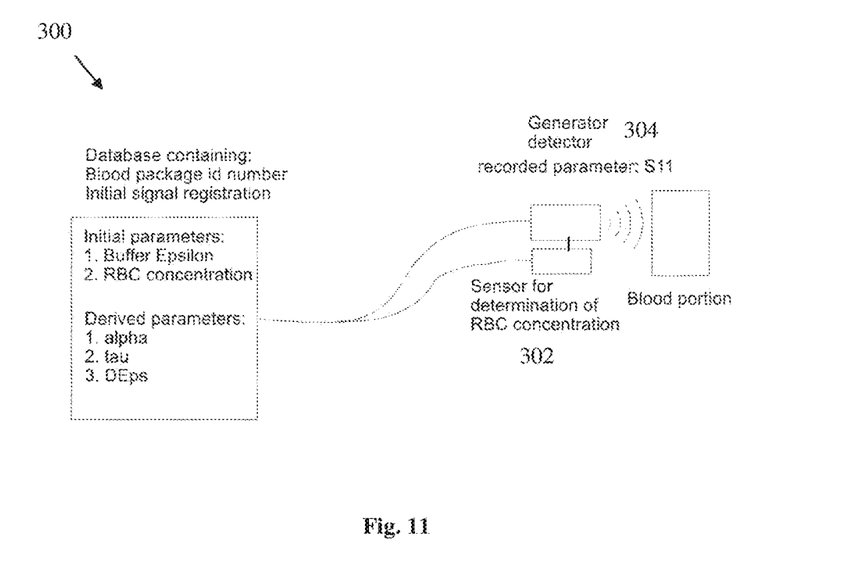
FIG. 11 schematically illustrates a blood bank inventory based on the recorded dielectric signal in the GHz range according to the principles of the present invention.

FIG. 11 schematically illustrates a blood bank inventory based on the recorded dielectric signal in the GHz range according to the principles of the present invention. In this specific and non-limiting example, the system 300 comprises inter alia an antenna 304 (noted as generator/detector) capable of generating at least one signal (e.g. set of signals), in the GHz range, that can sample the dielectric permittivity of the cytoplasm of the blood inside the sterile blood portion bag, non-invasively. The system 300 also comprises a control unit (e.g. PC database) and a sampling unit containing at least two sensors. The first sensor 302 is configured and operable used to determine the concentration of RBCs. Commercially available sensors may be used such as those made by Laser und Medizin Technologie GmbH of Berlin. Alternatively, the first sensor can be built using diffuse imaging in the near infrared (wavelength 700 nm-900 nm) [10]. The first sensor may also determine hemoglobin content by using the results of recent work made by Basey-Fisher et al. [11] suggesting that hemoglobin content can be established by DS in the microwave region. The second sensor is configured and operable to measure the reflection coefficient $S_{11}$, at a number of single frequencies in the region of 5 GHz to 60 GHz, straddling the main dielectric relaxation of bulk water. With the known dielectric spectrum of the background buffer, the contribution of the cytoplasm is extracted from Equation 1. The control unit extracts the dielectric parameters ($\alpha$, $\tau$, $\Delta\varepsilon$) from the resulting spectrum, or single frequency points, and compares to previously recorded values for the same blood portion. The rejection of the portion as viable depends on the acceptance criteria governing the acceptable values of the time derivative of the aforementioned parameters. By comparison of the measured signal with that of the buffer solution used to store the blood cells, the control unit provides a dielectric spectrum of the cellular cytoplasm (in accordance with the mixture formula in Equation (1)), at the frequency points measured. These points are then used to assess the changes in relaxation times or/and broadening of the peak. The control unit then compares these parameters against those recorded for the same blood sample at earlier times. The changes noted become the basis for the decision if the blood is viable or not. The initial measurement is made on the freshly deposited portion and this serves as the bench mark to judge the evolution of the sample.

The invention claimed is:
1. A system comprising:
   a sensor device configured and operable to non-invasively measure changes in a blood glucose concentration of a medium in a region of interest in a subject; said sensor device comprising at least one radiation sensor configured and operable to generate radiating beams of different frequencies toward the medium, receive radiation responses from the medium, and generate corresponding sensing data; and a control unit that is connectable to said sensor device and that is configured and operable to (i) select a frequency range of 0.5 GHz to 60 GHz; (ii) activate said sensor device to generate radiating beams of different frequencies in the selected frequency range; and (iii) receive and process the sensing data to determine a dielectric spectrum of the medium in said frequency range;

wherein said control unit is configured and operable to process the sensing data by (i) receiving a dielectric spectrum being indicative of bulk water; (ii) measuring a dielectric response of a blood-containing region in the frequency range of 0.5-60 GHz; (iii) extracting a spectrum of interest from the dielectric response of the blood-containing region and the dielectric spectrum indicative of bulk water; (iv) fitting the spectrum of interest to a Cole-Cole dielectric relation equation; (v) extracting from the spectrum of interest in said frequency range a broadening parameter of a main relaxation peak of the spectrum of interest and a relaxation time; and (vi) tracing a concentration-based behavior of the broadening parameter and the relaxation time.

2. The system of claim 1, wherein the radiation sensor comprises at least one antenna unit.

3. The system of claim 1, wherein the radiation sensor comprises at least one open resonator.

4. The system of claim 1, wherein said radiation sensor comprises at least one radiation unit, each radiation unit being configured and operable for sequentially generating two or more radiating beams of the different frequencies in said frequency range.

5. The system of claim 1, wherein said radiation sensor comprises a plurality of two or more radiation units configured and operable for generating a corresponding plurality of the radiating beams of the different frequencies in said frequency range.

6. The system of claim 1, wherein said radiation sensor is configured for location on a skin of a subject during measurements.

7. The system of claim 1, wherein said sensor device further comprises at least one sensor configured to determine at least one of blood volume, temperature and skin moisture.

8. The system of claim 1, wherein said control unit is configured and operable to determine the blood glucose concentration in the medium by fitting the spectrum of interest to the Cole-Cole dielectric function and a conductivity term as follows:

$$\varepsilon^*(\omega) = \frac{\Delta s}{1 + (i\omega\tau)^\alpha} + \frac{\sigma}{i\omega s_0} + \varepsilon_\infty$$

where $\Delta\varepsilon$ is a dielectric strength, $\tau$ is a characteristic relaxation time, $\alpha$ is the broadening parameter, $\sigma$ is a DC conductivity, $\varepsilon_0$ is a permittivity of free space and $\varepsilon_\infty$ is a high frequency limit of the real component of a dielectric permittivity.

9. The system of claim 1, wherein said control unit is configured and operable to extract a spectrum of a single red blood cell from the sensing data.

* * * * *